(12) United States Patent
Viellerobe et al.

(10) Patent No.: US 8,081,310 B2
(45) Date of Patent: Dec. 20, 2011

(54) MULTIMARKING FIBRE-TYPE FLUORESCENCE MICROSCOPIC IMAGING METHOD AND SYSTEM

(75) Inventors: Bertrand Viellerobe, Nogent sur Marne (FR); Florence Jean, Dampmart (FR); Genevieve Bourg-Heckly, Paris (FR); Alexandre Loiseau, Paris (FR)

(73) Assignee: Mauna Kea Technologies, Paris (FR)

( * ) Notice: Subject to any disclaimer, the term of this patent is extended or adjusted under 35 U.S.C. 154(b) by 619 days.

(21) Appl. No.: 11/629,213

(22) PCT Filed: Jun. 9, 2005

(86) PCT No.: PCT/FR2005/001424
§ 371 (c)(1),
(2), (4) Date: Dec. 12, 2006

(87) PCT Pub. No.: WO2006/000704
PCT Pub. Date: Jan. 5, 2006

(65) Prior Publication Data
US 2008/0029711 A1 Feb. 7, 2008

(30) Foreign Application Priority Data
Jun. 14, 2004 (FR) .................................. 04 06396

(51) Int. Cl.
*G01N 21/64* (2006.01)
(52) U.S. Cl. ...................................................... 356/417
(58) Field of Classification Search .......... 356/317–318, 356/417
See application file for complete search history.

(56) References Cited

U.S. PATENT DOCUMENTS

| 5,127,730 A | 7/1992 | Brelje et al. |
| 5,528,045 A * | 6/1996 | Hoffman et al. ............ 250/458.1 |
| 5,938,617 A * | 8/1999 | Vo-Dinh ........................ 600/476 |
| 6,066,459 A * | 5/2000 | Garini et al. ....................... 435/6 |
| 6,148,227 A | 11/2000 | Wagnieres et al. |
| 6,343,228 B1 | 1/2002 | Qu |
| 6,571,118 B1 * | 5/2003 | Utzinger et al. .............. 356/318 |
| 2003/0016897 A1 | 1/2003 | Walt et al. |
| 2003/0058440 A1* | 3/2003 | Scott et al. ...................... 356/318 |
| 2003/0220549 A1* | 11/2003 | Liu et al. ......................... 600/317 |
| 2004/0032651 A1 | 2/2004 | Storz et al. |
| 2005/0075575 A1* | 4/2005 | Vo-Dinh ........................ 600/476 |

FOREIGN PATENT DOCUMENTS

| JP | 2002267933 A | 9/2002 |
| JP | 2002267934 A | 9/2002 |
| WO | 0043552 A2 | 7/2000 |

(Continued)

OTHER PUBLICATIONS

Sabharwal et al. "Simultaneous 2-D analysis of multiple fluorescent probes using multispectral imaging microscopy", Jan. 1999, SPIE vol. 3603, pp. 122-128.*

(Continued)

*Primary Examiner* — Kara E Geisel
(74) *Attorney, Agent, or Firm* — Osha • Liang LLP

(57) ABSTRACT

The invention relates to a method for producing a fluorescent fiber image of a sample, wherein a sample is scanned with the aid of an excitation signal; the fluorescent signal emanating from the sample is detected, wherein the excitation signal and fluorescent signal use the same optical path; the optical path is used to excite at least two fluorophores contained in the sample; a final image is produced, including areas that are colored according to the at least two fluorophores. The multimarking according to the invention makes it possible to simultaneously acquire two images in two different wavelength bands. The system according to the invention can comprise a spectrometer for spectral quantification of the fluorescent signal.

28 Claims, 3 Drawing Sheets

FOREIGN PATENT DOCUMENTS

| | | |
|---|---|---|
| WO | 2003060493 A1 | 7/2003 |
| WO | 2004/010377 A2 | 1/2004 |
| WO | WO 2004/008952 * | 1/2004 |

OTHER PUBLICATIONS

Gmitro et al. "Confocal miscroscopy through a fiber-optic imaging bundle", Apr. 15, 1993, Optics Letters, vol. 18, No. 8, pp. 565-567.*

Japanese Office Action for Application No. 2007-526498, mailed on Jan. 25, 2011 (9 pages).

International Search Report issued in PCT/FR2005/001424, mailed on Oct. 31, 2005, 3 pages.

Rouse A R et al: "Multispectral Imaging with a Confocal Microendoscope" Optic Letters, Optical Society of America, Washington, US, vol. 25, No. 23, Dec. 1, 2000: pp. 1708-1710.

* cited by examiner

MULTIMARKING FIBRE-TYPE FLUORESCENCE MICROSCOPIC IMAGING METHOD AND SYSTEM

The present invention relates to a method and a system for producing a fluorescence fibre-type microscopic image of a sample. The field of application targeted is more specifically that of in vivo and in situ imaging.

The fluorescence observed can originate from an exogenous compound (typically an administered marker) or a compound produced by cells (of the transgenic marker type) of a biological tissue.

The document U.S. Pat. No. 6,148,227 describing a system of autofluorescence of tissues is known. A light beam excites an endogenous fluorophore of the tissue. The signal emitted is separated into a red signal and a green signal. These signals are then processed electronically in order to obtain a two-coloured image. The document U.S. Pat. No. 6,343,228 describes a fluorescence imaging system in which the fluorescence image is normalized using a reflectance image. The system comprises a first path for exciting the endogenous fluorophore of tissue and a second path for recovering the signal emitted by fluorescence and reflectance. The document WO 0043552 describes an integrated circuit, called a "biochip", the purpose of which is to detect several chemical compounds. This biochip comprises numerous sensors including a fluorescence detector. A laser or a light-emitting diode emits a light beam in order to excite a target element which, in response, generates a signal in an inherent manner or by injection of a suitable marker. The signal emitted can be a fluorescence, phosphorescence or Raman scattering signal. The optical paths between the incident flux and the signal emitted by the target element are different.

The drawback of the prior art described above is that none of these three documents makes it possible in particular to produce either a fibre-type confocal image or a high-resolution fibre-type image.

The present invention in particular relates to a fibre-type microscopic imaging system in which a sample is scanned using an excitation signal via an optical path, and the fluorescence signal originating from said sample is detected, the excitation signal and the fluorescence signal taking this same optical path. By contrast to the so-called table microscope, the microscopic imaging system, in particular in the field of endoscopy according to an application objective of the present invention, makes it possible to obtain an offset image retaining a microscopic resolution.

Finally, the document WO 2004/008952 from the relevant prior art may be mentioned, which proposes a method for producing an in vivo in situ confocal fluorescence image so as to optimize the quality of each image and obtain an excellent lateral and axial resolution. According to a first feature of this method for the production of a confocal image, an image guide is used made of several thousands of optical fibres which method consists of scanning point-by-point in a plane, in particular a subsurface plane, of a sample, each point corresponding to an excitation signal emitted by a continuous source, deflected and injected into one of the optical fibres of the beam then focussed, in particular using an optical head, at the output of the fibre in the plane, each point emitting in return a fluorescence signal collected by the optical fibre, then detected and digitized in order to form an image element. The confocal character is obtained by using the optical head to focus the beam in the sample, and by using as spatial filtering hole the same optical fibre to transport the excitation signal and the fluorescence signal emitted in response.

According to a second feature of this method for the production of a high-resolution fluorescence image, which is non-confocal compared to the first feature, in this case the end of the fibres is placed bare directly in contact with the surface of the sample to be imaged, each fibre being able to produce a divergent beam capable of exciting a micro-volume of the sample situated from the surface to a maximum depth depending in particular on the core diameter of the optical fibres. The images obtained are not "confocal" since they do not originate from a subsurface planigraphic plane scanned point-by-point. However they may be qualified as "highly resolved" images since they are produced by the scanning by turns of micro-volumes situated directly under the surface and by a spatial filtering of the fluorescence signal emitted by each micro-volume by the same fibre as that which served for the excitation.

In every case, for the two features, the excitation signal is deflected at a speed corresponding to the acquisition of a number of images per second sufficient for a real time use and the fluorescence signal is detected at a detection frequency corresponding to a minimum frequency of sampling of the fibres one-by-one. Respecting the sampling of the fibres (according to the Shannon criterion) makes it possible to obtain a point-by-point image which corresponds well to each fibre. This makes it possible to not lose information by sampling all of the fibres one-by-one while respecting a mean minimum number of images per second, namely in practice at least 12 images per second for a maximum mode of 896×640 pixels. The choice of the detection frequency (bandwidth of the detector) as a function of this minimum sampling then makes it possible for each fibre to detect the largest possible number of fluorescence photons. Thus, according to a possible embodiment, using an image guide with approximately 30,000 flexible optical fibres, the sampling frequency and the bandwidth of the detection system (an avalanche photodiode or equivalent) are set to approximately 1.5 MHz, corresponding approximately to 12 pixels per fibre, then making it possible to obtain at least the 12 images/s in maximum mode 896×640 pixels. In practice, the deflection of the beam is adjusted by determining a rapid resonance frequency of a "line" resonant mirror and a slow resonance frequency of a "frame" galvanometric mirror. This allows an appropriate rapid scanning of the fibres in order to obtain an image in real time.

The aim of the present invention is to enrich the information of the images obtained by a confocal fluorescence imaging system. Another aim of the invention is the monitoring of the behavioural development of clearly identified elements.

At least one of the above-mentioned aims is achieved with a method for producing a fibre-type fluorescence microscopic image of a sample, in which:
  the sample is scanned by means of an excitation signal via an optical path comprising at least one optical fibre, and
  the fluorescence signal originating from said sample is detected, the excitation signal and the fluorescence signal taking this same optical path.

According to the invention:
  at least two fluorophores contained in the sample are excited via the optical path,
  the fluorescence signal of each of said at least two fluorophores is detected via the optical path, and
  a final image is produced, said final image comprising areas which are coloured as a function of said at least two fluorophores.

The excitation signal can come from several other signals with different wavelengths.

The present invention thus makes it possible to carry out a multimarking, i.e. there are detected in the sample, which can be a human or animal tissue, at least two fluorophores, in other words dyes or markers. Each fluorophore emits a signal of a given wavelength when it is excited by a suitable light beam. Preferably, the fluorescence signals emitted by said at least two fluorophores have wavelengths which are sufficiently distant from one another so that these fluorescence signals can be split by spectral filtering. However when the fluorescence signals emitted by said at least two fluorophores have wavelength bands which are totally or partly superimposed on one another, splitting can occur, as will be seen below, by sequential emission, fine detection by filtering in the case of overlapping or sequential detection in the case of total superimposition.

With the method according to the invention, each fluorophore injected can mark a specific element. This fluorophore can effectively be administered (exogenous fluorophore) or be present in the sample from the start. The latter case comprises for example any transgenic animal expressing one or more fluorophores. The image obtained therefore makes these different elements appear with different colours. These colours can be arbitrary, i.e. "false" colours, or colours effectively corresponding to the wavelengths of the fluorescence signals emitted by the fluorophores. When viewing the image, in particular in real time, it is possible to monitor the evolution of the elements. For example it is possible to apply stimuli so as to view the reaction of each element. The multimarking makes it possible to obtain an image clearly distinguishing, by means of different colours, the different elements marked. The final image can comprise as many colours as injected fluorophores. Thus, a first fluorophore can have a morphological or spatial role, i.e. to mark the cell architecture for example, to show the skeleton, the container. A second fluorophore can have a functional role such as marking the proteins or ions so as to monitor their activity, and thus tracking the content. By way of example, it is possible to view the activity of calcium, marked by a first fluorophore, in neurons marked by a second fluorophore. For example it is possible to easily determine the nucleoplasmic index (core surface to cell surface) by marking one and the other with two fluorophores according to the invention. A person skilled in the art will easily understand that each fluorophore can have a functional or morphological role, etc.

The present invention can have numerous applications, in particular wherever non-invasive or slightly invasive methods are necessary. These applications are for example urethral endoscopy when an optical probe with a diameter less than 1 mm is inserted into a bladder for example; colonoscopy of small animals; viewing of the cornea and the retina; viewing of the muscle fibres and the nerves; microcirculation of leukocytes and blood flow; vascular and renal architecture; membranes of hepatic cells; and the in situ neurobiology for viewing of the deep brain structures of a small living animal for example.

According to an advantageous embodiment of the invention, said at least two fluorophores are excited simultaneously. Moreover, when the fluorescence signals of said at least two fluorophores are detected simultaneously, it is thus possible to work in real time, for example twelve images per second. The present invention thus allows an in vivo and in situ acquisition.

Alternatively, it is possible to sequentially excite said at least two fluorophores. The fluorophores are therefore excited one after the other. In the case where two fluorophores are injected and an image acquisition system in real time with twelve images per second is used, a final image is obtained at a rate of six images per second.

It is also possible to sequentially detect the fluorescence signals of said at least two fluorophores.

It is understood that the preferred implementation is therefore based on simultaneous emissions for simultaneous detections so as to obtain a final image in real time. By way of example, it is possible to use two laser emitters emitting at two different wavelengths in order to excite two fluorophores also emitting at two different wavelengths.

Advantageously, in every case, the sample is scanned at a speed corresponding to the acquisition of a number of images per second sufficient for a real time use. Moreover, the fluorescence signals are detected at a detection frequency corresponding to a minimum frequency of sampling of the fibres one-by-one. The scanning remains at the real time speed, it is the production of the final image which depends on the detection mode: simultaneous or sequential.

Preferably, in order to produce said final image, firstly as many primary images as detected fluorescence signals are produced, each primary image is coloured according to a colour assigned to the corresponding fluorophore, then said primary images are superimposed so as to make up the final image. The superimposition stage can also be a 50/50 merging or a transparency.

Moreover, it is also possible to acquire a spectrum (intensity as a function of the wavelength) of each image from a part of the signal originating from the sample via the optical path.

According to a variant and for a given image, a spectrum is also acquired from only one area of interest using a part of the signal originating from the sample via the optical path. The spectral analysis of a given area over time provides additional relevant information for the final image. It is thus possible to monitor and determine in an exhaustive manner the development of the marked elements as well as their reaction to stimuli.

In practice, in order to produce the spectrum, approximately twenty percent of the signal originating from the sample is sampled so as to not compromise the quality of the images.

According to the invention, said areas of interest are determined, prior to the acquisition of said spectrum, by carrying out a first image acquisition phase, then by defining said areas of interest on the image obtained.

Moreover, in order to acquire the spectrum only over areas of interest of an image, it is possible to use a switch usually called a "shutter", directing a part of the signal originating from the sample towards a spectrometer at predetermined times corresponding to times when the excitation signal scans said area of interest. Other high speed switches can be used such as a controlled mirror or an acousto-optic deflector.

It is also possible to use a high-frequency pulsed laser in order to emit the excitation signal, this pulsed laser being activated only for the scanning of said area of interest.

The subject of the present invention is also a system for producing a fibre-type fluorescence microscopic image of a sample, this system comprising:
 a processing unit,
 an optical path comprising at least means for scanning the excitation signal in the sample, an image guide comprising at least one optical fibre for conveying the excitation signal towards the sample and for collecting a fluorescence signal originating from said sample, the excitation signal and the fluorescence signal taking this same optical path.

According to the invention, the system also comprises:
- excitation means in order to excite, via the optical path, at least two fluorophores contained in the sample,
- detection means for detecting, via the optical path, the fluorescence signal of each of said at least two fluorophores, and
- processing means inside the processing unit in order to produce a final image comprising areas which are coloured as a function of said at least two fluorophores.

Preferably, the system according to the invention uses as a base, the device as described in the document WO 2004/008952 by Mauna Kea Technologies.

The scanning of the excitation signal can take place in a subsurface or surface plane or in a volume of the sample.

The excitation means can comprise an emitter, such as a laser for example, which is able to simultaneously excite said at least two fluorophores. In fact, laser devices exist, emitting in particular at 405 nm, which are capable of exciting two fluorophores at the same time. In this case, on receiving it is possible to arrange a photodetector detecting the fluorescence signals in a sequential manner, or two photodetectors (as many photodetectors as fluorophores) simultaneously detecting the fluorescence signals when the latter can be spectrally split.

Preferably, the excitation means include at least two emitters (two lasers in particular), which excite, simultaneously or sequentially, said at least two fluorophores. In this case, each emitter is preferably able to excite a single fluorophore.

Ideally as many emitters as detectors are arranged in order to simultaneously excite and detect and to produce an image in real time (twelve images per second).

The two emitters of excitation signals are advantageously two lasers emitting respectively at 488 nm and 635 nm, the two fluorophores in the sample reacting respectively to these two wavelengths.

In another embodiment, the detection means can comprise a receiver, such as a photodetector in particular, combined with a filtering means, a tunable band-pass filter for example, which allows each of the fluorescence signals emitted by said at least two fluorophores to pass sequentially.

But preferably, the detection means rather comprises at least two receivers combined with a separator such as a dichroic filter which is able to send, as a function of the wavelength, each fluorescence signal to a given receiver.

In a multi-path detection mode, several tunable band-pass filters and/or several tunable dichroic filters can be used. Similarly during emission, it is possible to use a single laser emitting simultaneously at several wavelengths.

Advantageously, the scanning means scan the sample at a speed corresponding to the acquisition of a number of images per second sufficient for a use in real time. Moreover, the detection means detect the fluorescence signals at a detection frequency corresponding to a minimum frequency of sampling of the fibres one-by-one.

According to a preferred embodiment, the image guide is constituted by several thousands of optical fibres, this guide being preceded by the scanning means and followed by an optical head in order to focus the excitation signal in the sample.

According to a variant embodiment, the image guide can be constituted by one optical fibre, the scanning means being integrated into the optical head situated between the image guide and the sample.

According to another variant embodiment, the image guide can be constituted by several thousands of optical fibres the distal ends of which are intended to be placed bare directly in contact with the surface of the sample. In this case, each fibre is able to produce a divergent beam capable of exciting a micro-volume of the sample situated from the surface to a maximum depth depending in particular on the core diameter of the optical fibres.

The system can also comprise a spectrometer which is able to produce a spectrum using a part of the signal originating from the sample. Thus a coupling between a fibre-type fluorescence imaging system, in particular confocal, and a spectroscopic analysis path is produced. This spectrometer can be combined with a shutter directing a part of the signal originating from the sample towards the spectrometer at predetermined times corresponding to the times when the excitation signal scans an area of interest. Alternatively, in order to acquire the spectrum only over an area of interest of an image, the excitation means can comprise at least one high-frequency pulsed laser, this pulsed laser being activated only during the scanning of said area of interest. It should be noted that the spectroscopy is also confocal when a confocal image acquisition system is used. It is also high resolution and non-confocal, when a high-resolution non-confocal image acquisition system is used.

According to the invention, the processing unit comprises means for synchronizing the excitation means and receiving means.

According to the invention, the image processing then carried out on the flux detected is optimized in order to obtain a very good quality image from the limited flux of photons detected. This optimization is carried out in the following manner.

A series of stages is carried out prior to the image acquisition in real time:
- a stage of detecting the location of each fibre of a chosen group of fibres intended to be used (either all of the image guide or a chosen sub-unit); this stage is to be carried out at least each time the image guide is changed;
- a stage of calibration of the rate of injection into each fibre, i.e. definition of an injection rate specific to each fibre; and
- a stage of detecting the background image (with no sample).

During operation, the optimization of the image processing in particular comprises the stages consisting of, after digitization of the signal detected:
- defining the real flux collected by each fibre i.e. originating only from the sample, after correction as a function of the injection rate specific to the fibre and subtraction of the background image, so as to obtain a corrected signal;
- then carrying out a reconstruction of the image from this corrected signal, in particular with the aim of converting an image having a mosaic of fibres into an image without noticeable fibres.

According to the invention, these last two stages are advantageously carried out in real time. As regards the correction of the signal, this can take place in real time thanks to a processing suited to the structure of the signal observed and an optimized algorithm. As regards the reconstruction of the image, it can take place by choosing a number of operations per pixel which can be carried out in real time making it possible to obtain the desired result in terms of image quality. A Gaussian low-pass filtering represents a good compromise between the complexity of the processing, the quality of the result and the calculation time.

Other advantages and characteristics of the invention will become apparent on examining the detailed description of an embodiment which is in no way limitative, and the attached drawings, in which.

Figure 1:
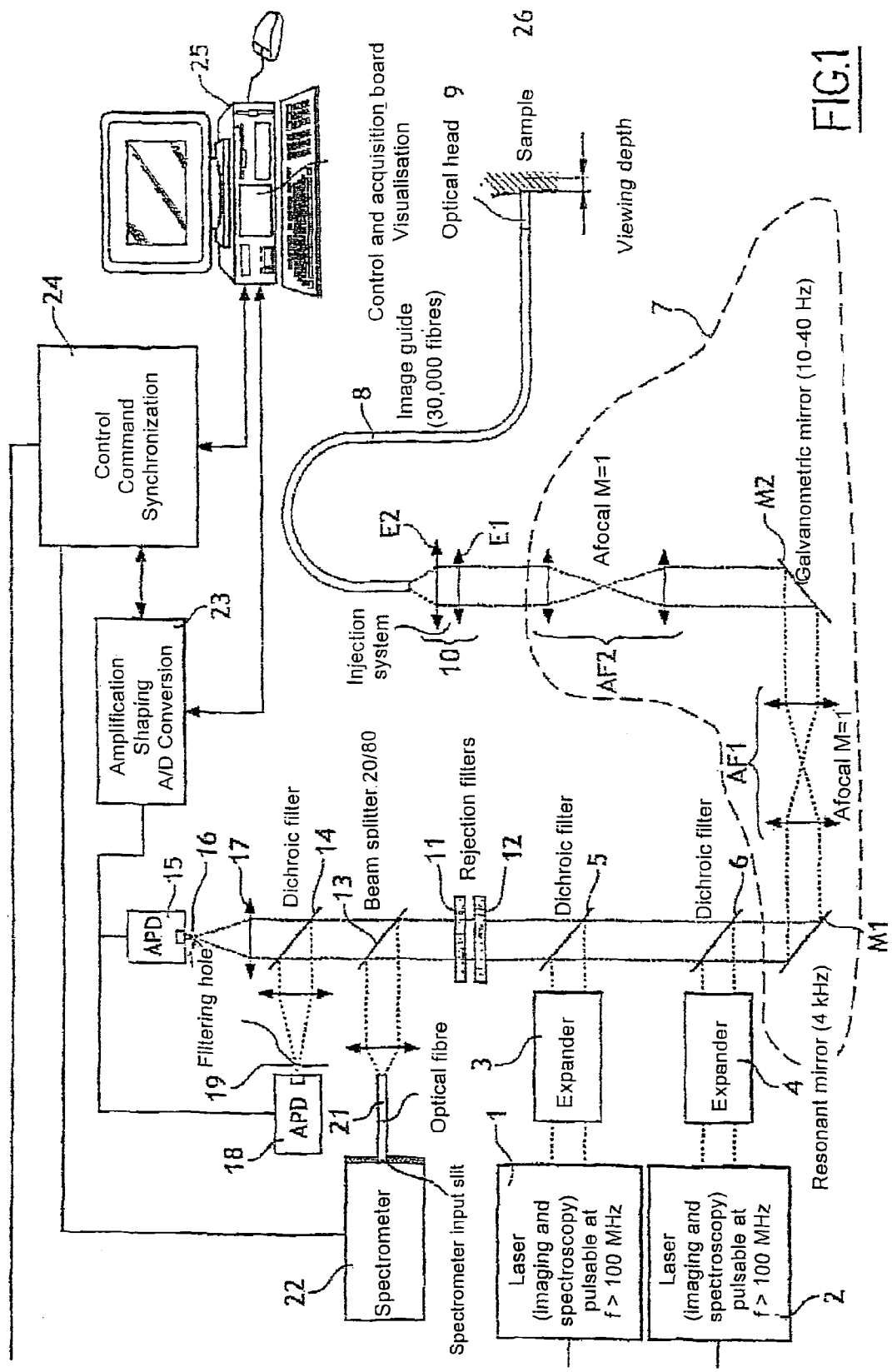
FIG. 1 is a diagrammatical view of the acquisition system according to the invention.

The system according to the invention for the production of high-definition confocal images in the case of two fluorophores present in the sample will now be described in a non-limitative manner. The latter can be a biological tissue or a cell culture.

The system comprises two excitation paths and two detection paths so as to effectively produce images in real time. For each path, the light source 1, 2 is a laser emitting at an excitation wavelength making it possible to excite a given fluorophore, for example 488 nm and 635 nm respectively. Each light source is able to excite one fluorophore. In order to optimize the injection into one of the fibres of the image guide 6, the excitation beam is circular in order to be able to inject a fibre also having a circular section and, in order to optimize the injection rate, the laser is preferably a single-mode longitudinal laser in order to have the best possible wave front for the injection into an optical fibre which is weakly multimode. The power available at the laser output is at least 20 mW. For the image acquisition, the laser can emit in a continuous and stable manner (the smallest possible noise, <1%). By way of example, a quantum well laser (VCSEL), a diode pumped solid laser, a laser diode or a gas laser such as an argon gas laser can be used. In the present case and as will be seen later, each laser can be used in pulsed mode at a frequency greater than 100 MHz, in order to produce spectroscopies only in the areas of interest.

At the output of the source 1, 2, the "expander" means 3, 4 for shaping the excitation laser beam are placed. They are constituted by an afocal optical magnification system different from 1, comprising lenses which allow modification of the diameter of the laser beam. The magnification is calculated such that the diameter of the beam is suited to the means of injection 10 into a fibre.

The reshaped excitation laser beam is then directed towards the means 5, 6 provided for separating the excitation and fluorescence wavelengths. These are for example a dichroic filter having a transmission efficiency of 98 to 99% at the excitation wavelength and which therefore substantially reflects the other wavelengths. The fluorescence signal, which takes upon returning the same optical path as the excitation signal, is thus sent towards the detection path 15, 18. The rejection means 11, 12, placed on the detection path serve to totally eliminate the 1 to 2% of stray reflections at the excitation wavelength 488 nm and 635 nm respectively, which pass towards the detection path (for example two rejection filters at 488 nm and 635 nm respectively).

The scanning means 7 then take up the excitation beam. According to the example chosen and represented in FIG. 1, these means include a resonant mirror M1 at 4 KHz serving to deflect the beam horizontally and therefore to produce the lines of the image, a galvanometric mirror M2 at 15 Hz, generally between 10 and 40 Hz, serving to deflect the beam vertically and therefore to produce the frame of the image; and two afocal unit-magnification systems, AF1 situated between the two mirrors and AF2 situated after the mirror M2, these afocal systems being used in order to conjugate the planes of rotation of the two mirrors M1 and M2 with the plane of injection into one of the fibres. According to the invention, the scanning speed is determined in order to allow an observation of the tissues in vivo in situ. For this purpose the scanning must be sufficiently rapid so that there are at least 12 images/s displayed on the screen for a display mode of 896×640 pixels corresponding to the slowest mode. For display modes having less pixels, the number of images acquired per second is thus still greater than 12 images/s. In a variant, the scanning means can comprise in particular a rotary mirror, integrated components of the MEM type (X and Y scanning mirrors), or an acousto-optic system.

The excitation beam deflected at the output of the scanning means is directed towards the optical means 10 in order to be injected into one of the fibres of the image guide 8. These means 10 are constituted here by two optical units E1 and E2. The first optical unit E1 allows partial correction of the optical aberrations at the edge of the field of the scanning means 7, the injection being thus optimized over all of the optical field (at the centre and at the edge). The second optical unit E2 is intended to carry out the injection itself. Its focal length and its numerical aperture have been chosen in order to optimize the rate of injection into the optical fibres of the guide 8. According to an embodiment which makes it possible to obtain the criterion of achromaticity, the first unit E1 is constituted by a doublet of lenses, and the second unit E2 by two doublets of lenses followed by a lens situated close to the image guide. In a variant, these injection optics could be constituted by any other type of standard optics, such as for example two triplets, or by lenses with a graded index (with a correction of the chromatism by diffractive optical elements) or by a microscope lens (which is however more costly).

The image guide 8 is constituted by a very large number of flexible optical fibres, for example 30,000 fibres of 2 μm diameter and spaced at intervals of 3.3 μm. In practice, it is possible to use either all of the fibres of the image guide, or a sub-unit chosen from these fibres, for example centred.

At the output of the optical fibre, the excitation laser beam is focussed by the optical head 9 in the sample 26 at a point situated at a given depth situated between a few tens of a μm and some one hundred μm, relative to the surface of the sample with which the optical head 9 is intended to be placed in contact with. This depth can be for example 40 μm. The optical head therefore makes it possible to focus the flux leaving the image guide into the sample, but also to collect the flux of fluorescence returning from the sample. The optical head has a magnification of 2.4 and a numerical aperture on the sample of 0.5. These two parameters are chosen so that the return signal only occurs in the optical fibre having transmitted the excitation signal and not in adjacent fibres and in order to thus preserve the confocal filtering using a fibre. With these magnification and numerical aperture values, the axial resolution is of the order of 15 μm and the lateral resolution of the order of 2 μm. The numerical aperture is also chosen in such a way as to optimize the number of photons recovered which must be as large as possible. The optical head can be constituted by standard optics (doublet, triplet, aspheric) and/or by lenses with a graded index (GRIN) having an optical quality and a chromatism suited to the confocality, i.e. minimizing the optical aberrations, which otherwise would lead, in particular, to degradations on the depth of field and as a result on the axial resolution of the apparatus. During operation, the optical head is intended to be placed in contact with the sample 26. The expression of the fluorescence is produced either by a fluorophore which is injected (systemic fluorescence), or by a fluorophore produced by the cell itself by modification of a gene (transgenic fluorescence). In the present case, the two fluorophores are injected and re-emit photons over a spectral band with a width comprised between 50 and 200 nm, in particular 100 nm.

On the detection path, at the output of the rejection filter 11, 12, the two fluorescence signals are separated, by wavelength selection, using a dichroic filter 14. Each fluorescence signal is then focussed by the means 17, respectively, constituted for example by a detection lens, in a filtering hole of the spatial filtering means 16, 19 respectively. The focal length of the detection lens is calculated such that the fluorescence signal originating from a fibre is of the same size or slightly smaller than that of the filtering hole. The latter makes it possible to retain the fluorescence light originating only from the fibre illuminated by the incident beam. It makes it possible to reject the light which could have been coupled in the adjacent fibres with the one which is illuminated. The size of the hole is calculated such that the image of a fibre is shown there perfectly. In this case, it is 20 μm.

The filters used have a bandwidth which is sufficiently selective to be able to separate the fluorescence signals and sufficiently large to be able to pick up a maximum number of photons necessary for a real time acquisition.

The detection means 15, 18 have a maximum sensitivity at the fluorescence wavelengths studied. It is possible for example to use an avalanche photodiode (APD) or a photomultiplier. Moreover, according to the invention, the bandwidth is chosen in order to optimize the integration time of the fluorescence signal. It is 1.5 MHz, which corresponds to the minimum sampling frequency of the image guide with an optimized integration time on each pixel.

The electronic and computational means 25 (such as a micro-computer) for control, analysis and digital processing of the detected signal and for viewing include the following boards:
- a synchronization board 24, the functions of which are:
  - to control in a synchronized manner the scanning, i.e. the movement of the line M1 and frame M2 mirrors;
  - to control in a synchronized manner with the fluorescence images, the spectral analysis of the data originating from a spectrometer 22;
  - to know at all times the position of the laser spot thus scanned; and
  - to manage all the other boards by means of a microcontroller itself being able to be controlled;
- a detector board 23 which comprises for each detection path an analogue circuit which in particular produces an impedance match, an amplifier, an analogue-to-digital converter then a programmable logic component (for example an FPGA circuit) which shapes the signal.

The micro-computer 25 also comprises a digital acquisition board (not represented) which makes it possible to process a digital data flow at variable frequency and to display it on a screen using a graphics board (not represented).

The system according to the present invention makes it possible to carry out an image processing such as described in particular in the document WO 2004/008952 and/or the document WO 2004/010377. This image processing makes it possible to obtain simultaneously in real time for each detection path, a primary image 27, 28 showing marked substances, see FIG. 2. The images 27, 28 and 29 correspond to a glandular tissue sampled by biopsy. More specifically, this tissue originates from a human thyroid. These images show glandular crypts. The present invention, with the system of FIG. 1, therefore allows the simultaneous acquisition of two images in two bands of different wavelengths.

The primary image 27 shows circular spots which are blue in colour. The blue colour is chosen in an arbitrary manner. These spots correspond to the fluorescence signals emitted by the first fluorophore called To-pro-3 and which is able to be excited by a laser beam at 635 nm. It is a DNA intercalating agent. This fluorophore makes it possible to identify the nucleus of a cell due to the presence of DNA in the nuclei.

The primary image 28 shows an arbitrarily red-coloured architecture, defining very specific spatial areas. These areas correspond to the fluorescence signals emitted by the second fluorophore called DiA and which is able to be excited by a laser beam at 488 nm. This fluorophore has an very strong affinity with the lipids (fatty acids) contained in the cell membranes of the cells. The visible areas on the images therefore correspond to the visible membranes in the image field. According to the invention, the two primary images are then superimposed in order to form a final image 29 showing, in FIG. 2, both the blue and red elements. This makes it possible to better delimit the blue nuclei inside the red membranes.

Figure 3:
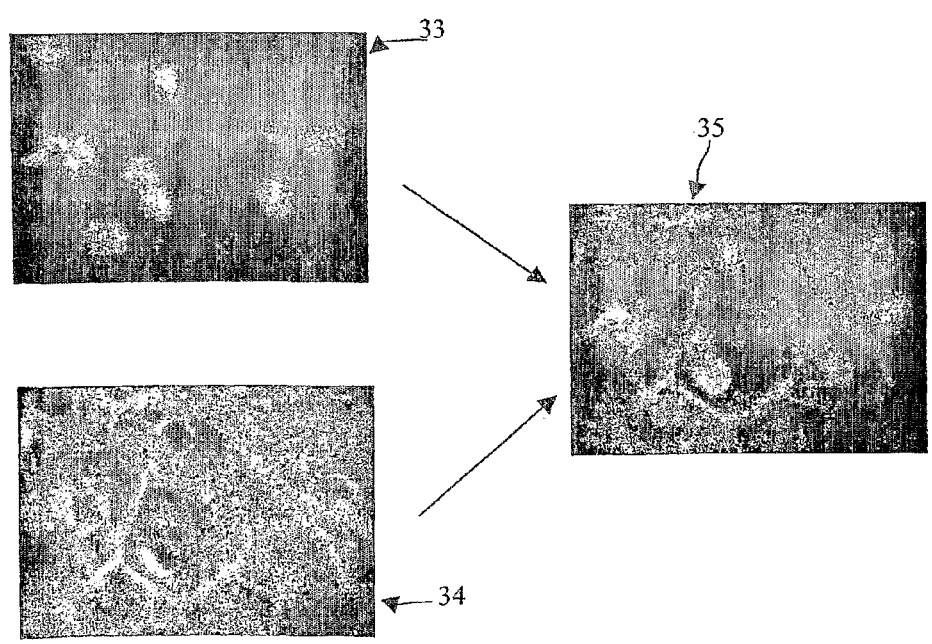
FIG. 3 is also a diagrammatical view illustrating the production of another final image according to the invention from two other primary images each showing elements coloured by a given fluorophore.

In the same way, in FIG. 3, the images 33, 34 and 35 represent a malpighian tissue originating from a cervix uterus. In image 33, the visible spots, coloured blue, correspond to the DNA of the cell nuclei. The marker used is POPO-1 excited at 405 nm. In FIG. 34, the "honeycomb" structure, coloured red, corresponds to the nuclear and cell membranes. The marker used is DiA excited at 488 nm. In image 35, the superimposition of the two images 33 and 34 is seen. The nuclei inside their cell membrane are clearly seen.

Advantageously, the fluorescence image acquisition paths are coupled to a spectral path. The spectrometer 22 in FIG. 1 makes it possible to carry out a spectral analysis of all or part of an image.

The temporal and spectral monitoring of a fluorescence signal can provide very important information on the functional biochemical activity of a biological tissue. In fact, the fluorophores used to produce the fluorescence image or images are very sensitive to their close environment (in particular "intelligent" fluorophores can be chosen which react in particular to changes in their immediate environment or which interact specifically with very specific molecular species). The level of their fluorescence (intensity) and the form of their fluorescence (spectrum) vary as a function of the changes which occur in the surrounding environment. The study over time of the intensity and the spectrum of the fluorescence therefore provides information on the dynamics of the biological environment. In this case, monitoring the action of a medication or monitoring the metabolic activity or monitoring the action of an external stress (change of pH, temperature, enzyme activity, etc.) can be recorded thanks to the spectral and temporal analysis of the fluorescence. The advantage of such a coupling resides in particular at the level of the more detailed analysis of the fluorescence. Several cases of analysis can be envisaged:
- the temporal and spectral monitoring of the fluorescence of an image: in this case, the spectral analysis applies to all of the image. This is a first fairly crude analysis of the area observed as a whole;
- the temporal and spectral analysis of the fluorescence of an area of interest of an image: this case, which is of much greater interest, represents the analysis of a specific area of the image. It is therefore necessary to carry out an analysis beforehand of the confocal fluorescence image in order to determiner the so-called areas "of interest" and then to carry out the spectral analysis of these areas. It is therefore necessary to synchronize the analysis by the image and the spectral analysis; and the temporal and spectral monitoring of the autofluorescence of an image: in the latter case, this is the analysis of the autofluorescence of the tissue. In this particular case, a laser is used in blue part of the spectrum. Moreover, the fluorescence induced by exogenous fluorophores must not prevent the detection of the autofluorescence (which is quite weak). The autofluorescence corresponds to the flux originating from naturally fluorescent compounds such as flavin, NADH, porphyrin, etc. present in living tissues.

In particular in the second case, it is necessary to analyze the images (acquisition, processing, identification of the areas of interest), to synchronize the spectroscopy path with the passage over the areas of interest and finally to analyze the corresponding spectrum. The implementation of the coupling in this second case is envisaged according to two variants: a pulsed laser mode and a high speed switching mode.

Figure 2:
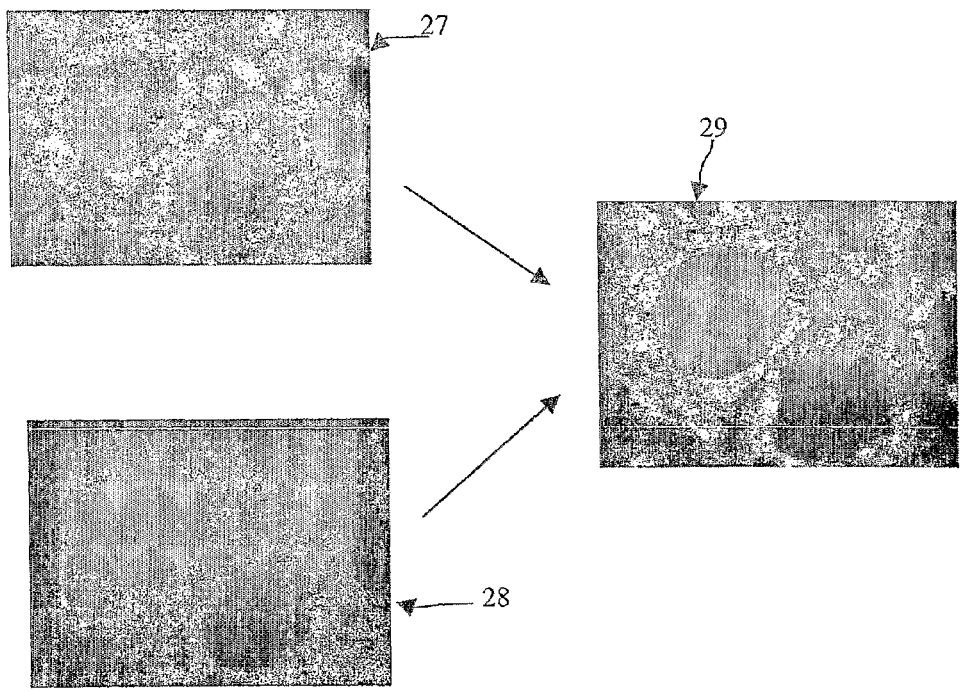
FIG. 2 is a diagrammatical view illustrating the production of a final image according to the invention from two primary images each showing elements coloured by a given fluorophore.

FIG. 1 shows the case of the use of pulsed lasers in order to excite the sample and thus to obtain an image and a spectrum of a whole image or of a region (or regions) of interest. The fact of using a pulsed laser makes it possible to avoid additional losses introduced by the addition of a component on the spectroscopy path as will be seen in the high speed switching mode. A beam splitter 13 samples twenty percent of the light flux originating from the rejection filters 11, 12. The flux sampled is then introduced into an optical fibre 21 supplying the spectrometer 22.

In this case, it is therefore sufficient to switch the laser on only in the so-called areas of interest and to detect the spectrum associated with these areas. This is simply a synchronization regarding the illumination of the tissue which can be carried out simply by computational means. This solution is the most simple to implement.

Figure 4:
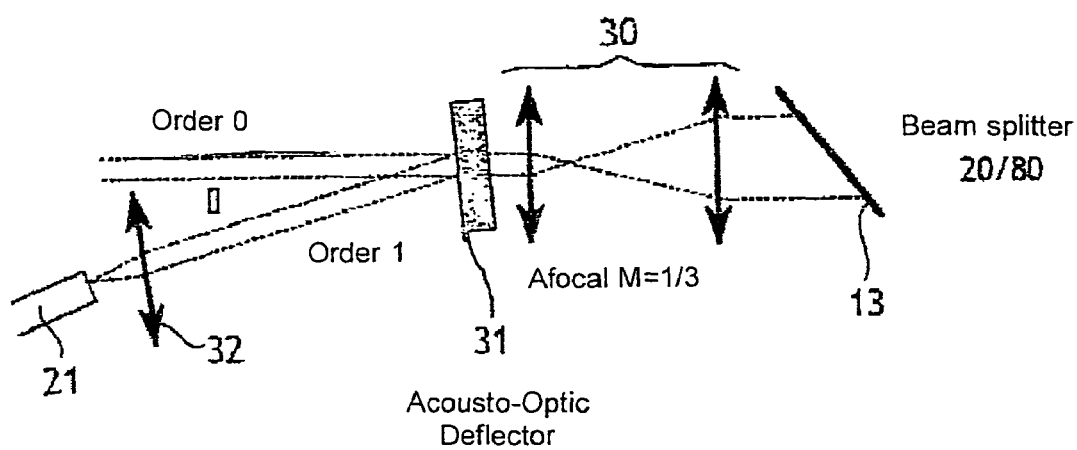
FIG. 4 is a diagrammatical view of an acousto-optic switch.

The high speed switching mode calls for the use of a very high speed filtering system placed at the input of the spectroscope (see FIG. 4). It is then possible to direct the fluorescence flux towards the spectroscope when the position of the laser scanning corresponds to the passage over the areas of interest in a very short time. Ideally, the device must switch to each fibre, i.e. a time of 1 µs (a line of fibre is scanned at a speed of 1 µs/fibre). In practice, the flux of a nucleus (5 µm at the level of the tissue) is integrated for example, which corresponds to an integration time of a few µs at maximum. As is seen in FIG. 4, the components of this spectroscopy path are the following:
  the beam splitter 13 with an 80% transmission coefficient for the imaging path and a 20% reflection coefficient for the spectroscopy path, in order not to reduce too much the flux necessary in order to form an image;
  A device 31 which is sufficiently high speed to switch to each fibre scanned or onto an area (or areas) of interest defined previously. It can be mechanical, acousto-optic (31), a mirror, etc.;
  An achromatic doublet 30 with a focal length of 100 mm in order to focus the beam in the optical fibre.
  An optical fibre 21, with a core diameter of 50 or 100 µm as a function of the desired resolution, with a numerical aperture of 0.22; and
  A spectroscope 22, the characteristics of which are the following: firstly, a detector composed of a linear CCD (2048 pixels) or a matrix CCD for example, with a range of wavelengths comprised between 200 and 1100 nm, with a sensitivity of 86 photons/count ($2.9 \times 10^{-17}$ W/count) and with a signal to noise ratio of 250:1. Secondly, a diffraction grating with 600 lines/mm, with an efficiency greater than 30%, with a resolution comprised between 0.3 nm and 10.0 nm FWHM and finally with a slit width of 200 µm.

Several devices for high speed can be envisaged:
  1) A mechanical "shutter": in this case it is a plate driven in movement by a translation plate which is motorized in order to allow the beam to pass when an area of interest is scanned. The translation plate must have a resolution of a few tens of micrometers, being driven by a stepping motor or a DC motor, a travel of a few millimetres. Its reaction speed depends on the size of the area of interest, it is preferably very significant.
  2) A mirror: another switching device consists in deflecting the beam when the scanning is outside of an area of interest, in order to reject the signal "outside of the area of interest". For this purpose, a mirror is used, placed after the beam splitter, and having a response time of the order of a microsecond for an angle of a few milliradians at minimum, and a high reflection rate. The spectroscopic path therefore no longer operates in transmission but in reflection.
  3) An acousto-optic deflector according to FIG. 4. The components necessary for this configuration are: an afocal system 30 with ⅓ magnification comprising two achromatic doublets in order to reduce the size of the beam in order to enter the deflector 31 the opening of which is 2 mm. This deflector operates on the spectral range 400-800 nm with a response time of less than a microsecond (in order to switch to each fibre if possible). The deflection efficiency is 90% and the static losses are minimized (<10%) in order not to have to too greater losses in transmission and a deflection angle of a few milliradians. Finally, the focusing optics 32 is placed in the direction of deflection (order 1), because the deflection efficiency is 90% (there is still 10% of the flux in the direction of the order 0).

In every hypothetical case ("shutter" solution or pulsed laser solution), it is possible to envisage computer (automatic) plug-ins capable of tracing the reduction of a fluorescence peak as a function of the time or the evolution of the ratio between two fluorescence peaks in time and space. These are technical modules produced to suit the needs of the users.

The choice of the areas of interest is made either by the user, or automatically.

Of course, the invention is not limited to the examples which have just been described and numerous adjustments can be made to these examples without exceeding the scope of the invention. It is possible to envisage the production of a high-resolution non-confocal image, using a guide constituted by several thousands of optical fibres the distal ends of which are intended to be placed bare directly in contact with the surface of the sample. In this case it is possible in particular to use the teachings of the document WO 2004/008952 adapted according to the present invention.

The invention claimed is:
1. A method for producing a fiber-type fluorescence microscopic image of a sample that contains at least two fluorophores, comprising:
  scanning the sample with an excitation signal via an optical path comprising a plurality of optical fibers, wherein the scanning injects the excitation signal into one optical fiber at a time,
  detecting fluorescence signals originating from the at least two fluorophores in said sample,
    wherein the excitation signal and the fluorescence signals take the same optical path,
    wherein the at least two fluorophores contained in the sample are excited via the same optical path, wherein the fluorescence signals of said at least two fluorophores are detected via the same optical path; and producing a final image comprising areas which are colored as a function of said at least two fluorophores.

2. The method according to claim 1, wherein said at least two fluorophores are excited simultaneously.

3. The method according to claim 1, wherein said at least two fluorophores are excited sequentially.

4. The method according to claim 2, wherein the fluorescence signals of said at least two fluorophores are detected simultaneously.

5. The method according to claim 3, wherein the fluorescence signals of said at least two fluorophores are detected sequentially.

6. The method according to claim 1, wherein the scanning the sample is performed at a speed corresponding to acquisition of a number of images per second sufficient for a real time use, and wherein the fluorescence signals are detected at a detection frequency corresponding to a minimum frequency for sampling the at least one optical fiber one-by-one.

7. The method according to claim 1, wherein in order to produce said final image, as many primary images as detected fluorescence signals are produced, each primary image is colored according to a color assigned to the corresponding fluorophore, then said primary images are superimposed so as to make up the final image.

8. The method according to claim 1, wherein a spectrum of each image is also acquired using a part of the fluorescence signals originating from the sample via the optical path.

9. The method according to claim 1, wherein, for a given image, a spectrum of an area of interest is also acquired using a part of the fluorescence signals originating from the sample via the optical path.

10. The method according to claim 9, wherein said areas of interest are determined, prior to the acquisition of said spectrum, by producing a first image acquisition phase, then by defining said areas of interest on the image obtained.

11. The method according to claim 9, wherein in order to acquire the spectrum only on areas of interest of one image, a shutter is used directing a part of the fluorescence signals originating from the sample towards a spectrometer at predetermined times corresponding to the times when the excitation signal scans said area of interest.

12. The method according to claim 9, wherein, in order to acquire the spectrum only over one area of interest of one image, at least one high-frequency pulsed laser is used in order to emit the excitation signal, this pulsed laser being activated only for the scanning of said area of interest.

13. A system for producing a fiber-type fluorescence microscopic image of a sample, comprising:
a processing unit;
an optical path comprising a scanner for scanning an excitation signal into the sample, an image guide comprising a plurality of optical fibers for conveying the excitation signal towards the sample and for collecting a fluorescence signal originating from said sample, the excitation signal and the fluorescence signal taking the same optical path, wherein the scanner is configured to inject the excitation signal into one optical fiber at a time;
a light source in order to excite, via the optical path, at least two fluorophores contained in the sample,
a detector for detecting, via the optical path, fluorescence signals of each of said at least two fluorophores, and
a processor inside the processing unit in order to produce a final image comprising areas which are colored as a function of said at least two fluorophores.

14. The system according to claim 13, wherein the light source includes an emitter capable of simultaneously exciting said at least two fluorophores.

15. The system according to claim 13, wherein the light source includes at least two emitters, each exciting one of said at least two fluorophores.

16. The system according to claim 15, wherein the fluorescence signals emitted by said at least two fluorophores have wavelengths which are sufficiently distant from one another so that the fluorescence signals can be separated by filtering.

17. The system according to claim 15, wherein the two emitters of excitation signals are two lasers emitting respectively at 488 nm and 635 nm, the two fluorophores in the sample reacting respectively to these two wavelengths.

18. The system according to claim 13, wherein the detector comprises a receiver combined with a tunable filter.

19. The system according to claim 13, wherein the detector includes at least two receivers combined with a separator which is able to send, as a function of the wavelength, each of the fluorescence signals towards a given receiver.

20. The system according to claim 13, wherein the scanner scans the sample at a speed corresponding to acquisition of a number of images per second sufficient for a real time use and the detector detects the fluorescence signals at a detection frequency corresponding to a minimum frequency for sampling the at least one optical fiber one-by-one.

21. The system according to claim 13, wherein the image guide comprises several thousands optical fibers, the image guide being preceded by the scanner and followed by an optical head in order to focus the excitation signal in the sample.

22. The system according to claim 13, wherein the scanner is integrated into an optical head situated between the image guide and the sample.

23. The system according to claim 13, wherein the image guide is constituted by several thousand optical fibers, the distal ends of which are configured to be placed bare directly in contact with a surface of the sample.

24. The system according to claim 13, further comprising a spectrometer which is able to produce a spectrum using a part of the fluorescence signals originating from the sample.

25. The system according to claim 24, wherein the spectrometer is combined with a shutter directing a part of the fluorescence signals originating from the sample towards the spectrometer at predetermined times corresponding to the times when the excitation signal scans an area of interest.

26. The system according to claim 24, wherein, in order to acquire the spectrum only on an area of interest of an image, the light source includes at least one high-frequency pulsed laser, this pulsed laser being activated only during the scanning of said area of interest.

27. The system according to claim 13, wherein the processing unit comprises means for synchronization of the light source and the detector.

28. The system according to claim 18, wherein the tunable filter is a tunable band-pass filter, which allows each of the fluorescence signals emitted by said at least two fluorophores to pass sequentially.

* * * * *